United States Patent [19]
Krstanovic

[11] Patent Number: 5,494,641
[45] Date of Patent: Feb. 27, 1996

[54] CONNECTORIZED CAPILLARIES FOR USE WITH SEPARATION INSTRUMENTATION COMPONENTS

[75] Inventor: Srdjan Krstanovic, Windham, N.H.

[73] Assignee: Orion Research, Inc., Boston, Mass.

[21] Appl. No.: 346,341

[22] Filed: Nov. 29, 1994

Related U.S. Application Data

[63] Continuation of Ser. No. 31,007, Mar. 12, 1993, abandoned.

[51] Int. Cl.$^6$ .................................................. B01L 11/00
[52] U.S. Cl. ..................... 422/103; 422/99; 73/861.08; 204/604; 285/911; 285/342; 285/343; 96/106
[58] Field of Search .................... 422/99, 100, 103, 422/104; 204/299 R, 180.1, 182.8; 285/911, 915, 342, 343; 210/656, 198.2; 73/861.08; 96/106

[56] References Cited

U.S. PATENT DOCUMENTS

| | | | |
|---|---|---|---|
| 3,819,212 | 6/1974 | St. John et al. | 285/356 |
| 3,880,452 | 4/1975 | Fields | 285/177 |
| 3,992,043 | 11/1976 | Whitley | 285/342 X |
| 4,083,702 | 4/1978 | Hartigan et al. | 55/67 |
| 4,116,837 | 9/1978 | Biermacher | 210/198.2 |
| 4,136,897 | 1/1979 | Haluch | 285/342 |
| 4,394,263 | 7/1983 | Dosch et al. | 210/198.2 |
| 4,529,230 | 7/1985 | Fatula, Jr. | 285/341 |
| 4,669,763 | 6/1987 | Phillips | 422/99 X |
| 4,690,437 | 9/1987 | Anderson, Jr. | 285/911 X |
| 4,708,782 | 11/1987 | Andresen et al. | 210/656 X |
| 4,787,656 | 11/1988 | Ryder | 285/177 |
| 4,792,396 | 12/1988 | Gundelfinger | 210/656 X |
| 4,991,883 | 2/1981 | Worden | 285/342 X |
| 5,131,998 | 7/1992 | Jorgenson et al. | 210/656 X |
| 5,188,730 | 2/1993 | Kronwald | 210/198.2 |
| 5,211,221 | 5/1993 | Lease | 285/915 X |
| 5,234,235 | 8/1993 | Worden | 285/342 X |
| 5,288,113 | 2/1994 | Silvis et al. | 285/342 |

FOREIGN PATENT DOCUMENTS

| | | |
|---|---|---|
| 3926687 | 2/1991 | Germany . |
| 2049976 | 12/1980 | United Kingdom . |

OTHER PUBLICATIONS

Kucera, P. et al. "Use of Open–Tubular Columns in Liquid Chromatography", *Journal of Chromatography*, vol. 283, 1984.

*Primary Examiner*—James C. Housel
*Assistant Examiner*—Maureen M. Wallenhorst
*Attorney, Agent, or Firm*—Ernest V. Linek

[57] ABSTRACT

A connectorized capillary and in-line flow cell system which greatly expedites the construction of capillary zone electrophoresis (CZE) and other separation instrumentation. A capillary is mounted within a cavity formed in a body, and a mechanical fastener is positioned about the body. The inner diameter of the fastener is less than the outer diameter of the body, so that the connector may be firmly coupled to any system component having a corresponding portion adapted to accept the fastener. The connectorized capillaries thus permit permanent or semi-permanent attachment to various in-line flow cell devices such as detectors, valves, buffer reservoirs and the like. For example, an in-line conductivity detector is assembled by connecting a conductivity meter to the opposing ends of the flow cell body. Annular sensing surfaces can also be provided within the cell. The same basic flow cell structure can also be used as a discrete separation valve by forming two transverse openings in the flow cell body and by using a ferrule having a slotted or castleated end. The valve can be electrically operated by switching a ground reference electrode between two or more buffer reservoirs. The same connectorized capillaries may also be used with fused plate-type systems containing etched channels.

16 Claims, 15 Drawing Sheets

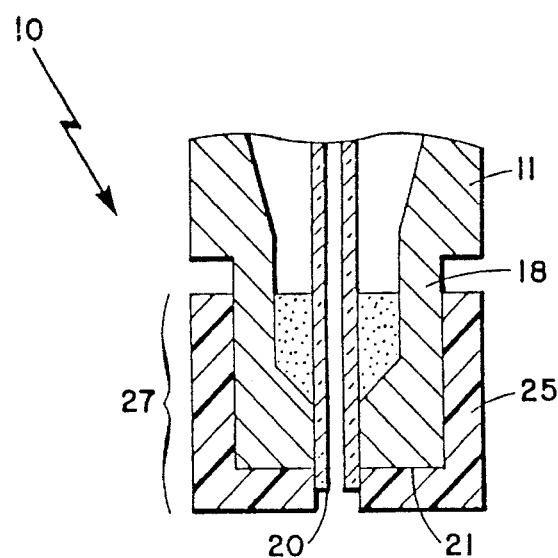
_Fig. 2A_
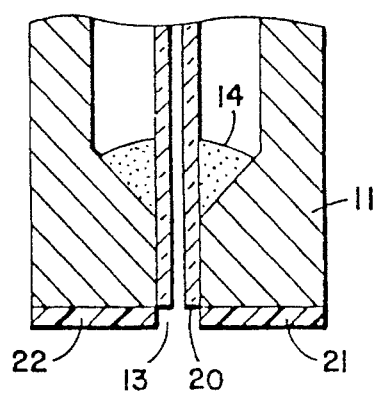
_Fig. 2B_
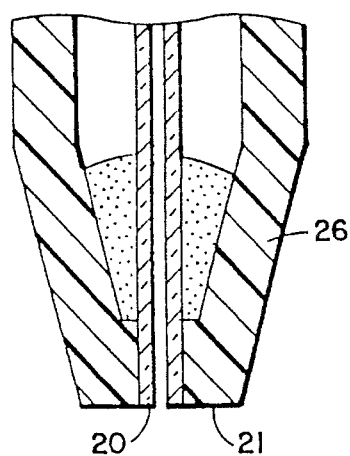
_Fig. 2C_

CONNECTORIZED CAPILLARIES FOR USE WITH SEPARATION INSTRUMENTATION COMPONENTS

This application is a continuation of application Ser. No. 08/031,007, filed on Mar. 12, 1993 and now abandoned.

FIELD OF THE INVENTION

This invention relates generally to analytical instrumentation and more specifically to a technique for interconnecting the various components of a separation analysis instrument.

BACKGROUND OF THE INVENTION

Scientific researchers often require the identification of the constituent parts of chemical and biological samples. For example, particular experiments may require determination of the homogeneity, identification of proteins, or even the mapping of nucleic acid structures such as DNA and RNA.

The instruments used to perform such analyses typically operate on the principle that molecular species can be isolated from one another by capitalizing on the fact that each species has a unique combination of mass, size, shape, charge, mobility, density, sub-unit structure, or optical emission, absorption, or reflectance. Liquid chromatography (LC), super critical fluid chromatography (SFC), gas chromatography (GC) and capillary zone electrophoresis (CZE) are among the most commonly used separation techniques that take advantage of one or more of these differences in molecular properties.

Capillary zone electrophoresis, for example, makes use of the fact that different ionic species have different mobilities when subjected to an electric field. In a CZE instrument, an extremely thin capillary tube is typically filled with a conductive buffer solution. A small amount of the sample to be analyzed is then introduced into the buffer solution at an inlet end of the capillary tube, and an electrical potential difference is applied across the ends of the tube. The resulting electric field causes the various ions in the sample to begin migrating down the tube. Because of differences in the electrophoretic mobilities of different ions, the various constituents of the sample exit the outlet end of the tube at different times, and in groups of like ions, or so-called 'zones'. The chemical or biological makeup of a sample can thus be detected by determining the timing and the concentration of the zones exiting from the tube.

In CZE and similar instruments which rely on separation techniques, it is often advantageous or necessary to connect capillary tubes together. Likewise, it is often necessary to connect capillary tubes to various structures such as detectors, fluid valves, and buffer solution reservoirs, to further process and separate the samples.

A problem generally exists with such apparatus, since the user cannot readily change a particular configuration. For example, researchers often may wish to compare the results when the size of capillary tube is changed, with coated and uncoated tubes, with detectors of different types, and with different flow cells. Furthermore, the optimum configuration of these components typically also depends upon the nature and desired accuracy of the particular information being sought.

It is thus desirable to provide a separation instrument which would permit the user to efficiently connect and disconnect the many operational components such as conductivity, electrochemical, ultraviolet/visible (UV/VIS), and fluorescence detectors of various types, as well as buffer solution reservoirs, and valves.

However, probably because of the extremely small tolerances involved, this has heretofore been thought to be difficult to achieve. For example, the capillary tubes used in CZE instrumentation typically have an outer diameter on the order of 150 to 360 microns, and nominal inner diameters of 50 to 75 microns or less with tolerances as small as a few microns being required in some applications. And yet, the capillary tubes must be accurately aligned with a detector, for example, to avoid creating adverse effects.

U.S. Pat. No. 4,787,656 issued to Ryder and assigned to Hewlett Packard Company discusses a coupling device for connecting capillary tubing. While the coupling device can be used to connect two pieces of tubing together, it is not readily apparent how such a device could be adapted, or that it is even desirable, to permit detachment as well as attachment of capillaries, or how one would provide a quick and easy mechanism for interconnecting various components of an analytic instrument.

SUMMARY OF THE INVENTION

It is an object of this invention to provide an interconnection device for the various components of a separation instrument. The mechanisms should afford ease of connecting and disconnecting capillaries to one another as well as to various system components such as detectors, buffer reservoirs, valves, and other in-line devices such as flow cells.

Briefly, an apparatus constructed in accordance with the invention makes use of a connectorized capillary system in which the capillary is mounted within a cavity formed in a body. A nut or bayonet having a collar is positioned about the body. The inner diameter of the collar is less than the outer diameter of the body, so that the connector may be firmly coupled to any system component having a corresponding threaded, bayonetted, or similar connector portion.

The capillary is held firmly and accurately in position inside the body by an epoxy or other fixing means such as a compression fitting.

The connectorized capillaries thus permit permanent or semi-permanent attachment of capillaries to various in-line instrumentation components such as detectors, valves, buffer reservoirs and the like.

The ends of the connectors may have sealing surfaces or carry ferrules to prevent fluid leaks, and may be tapered to expedite self-centering for use with plate-type interconnection devices.

The basic instrument component is constructed by attaching capillaries to a body having an axially oriented fluid transmission cavity with threaded, bayoneted, or similar fasteners on opposing ends.

An in-line conductivity detector flow cell is assembled for example from the basic component by connecting a conductivity meter to opposing ends of the flow cell bodies. Annular sensing surfaces within the cell are provided by appropriately positioning the capillaries with respect to the cell bodies or by forming an annulus on the end of the connector bodies. In addition, various types of gaskets can be used to provide different detector geometries.

The same basic structure can also be used as a discrete separation valve by forming a transverse opening in the flow cell body and by using a connector body having a slotted or castleated end. The valve can be electrically operated by switching a ground reference electrode between two of more buffer reservoirs. Similarly, the valve can be hydrostatically operated by initiating flow across the transverse opening, thus sweeping out ions emerging from the capillaries.

The connectorized capillaries may also be used with plate-type system components which have been fitted with surface-mountable receptacles. The plate components provide alternate means for implementing detectors and other instrumentation system components.

BRIEF DESCRIPTION OF THE DRAWINGS

The novel features believed to be characteristic of the invention are pointed out in the appended claims. The best mode for carrying out the invention and its particular features and advantages can be better understood by referring to the following detailed description, when read together with the accompanying drawings, in which:

FIGS. 2A through 2C are cross-sectional views illustrating the outlet end portions of various connectorized capillaries in greater detail;

DETAILED DESCRIPTION OF A PREFERRED EMBODIMENT

Figure 1A:
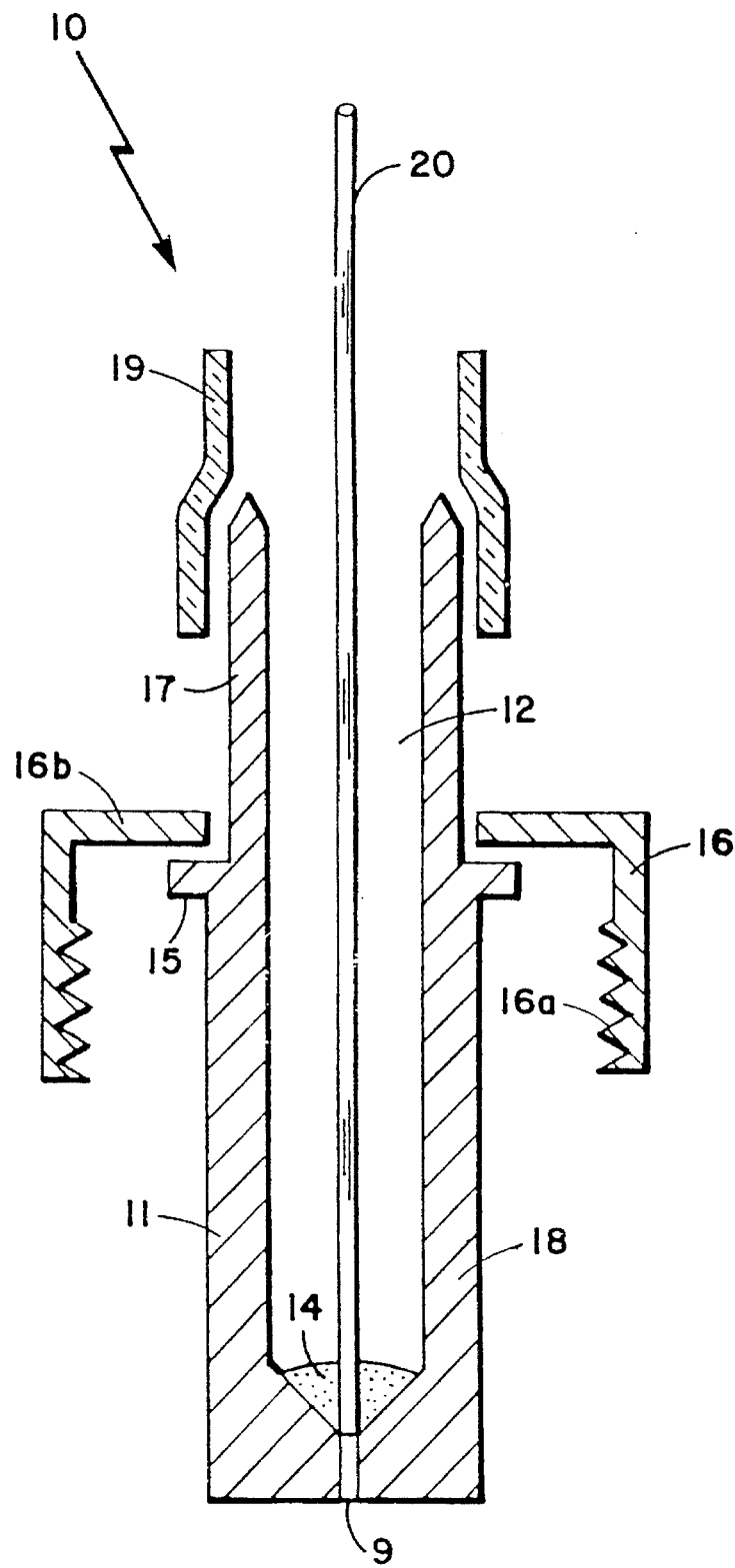
FIG. 1A is a cross-sectional view showing a connectorized capillary according to the invention.

FIG. 1 is a cross-sectional view of a connector 10 for a capillary tube 20 according to the invention. The connector 10 consists of a body 11 having a cavity 12 formed therein.

The body 11 is typically formed from stainless steel, zirconium, polytetraflouroethylene (PTFE) or other material formulations, depending upon whether the connector 10 is intended to be electrically insulating or electrically conductive, heat resistant, sealing and so forth. Although the connector 10 and other system components are described below as typically being round in cross-section, it should be understood that the invention may be embodied in other cross-sectional shapes, including square, rectangular, hexagonal, and the like.

The body 11 is divided into a lower portion 18 and upper portion 17, the lower portion 18 typically having a greater outer diameter than an upper portion 17. At the lower body portion 18, the cavity 12 tapers to a small opening or outlet 9 which is of the same approximate diameter as the outer diameter of the capillary tube 20. A securing means 14 such as an epoxy, glue, cement, or other fixing material is disposed in the cavity 12 about the capillary 20 to hold the capillary 20 in place.

Figure 1B:
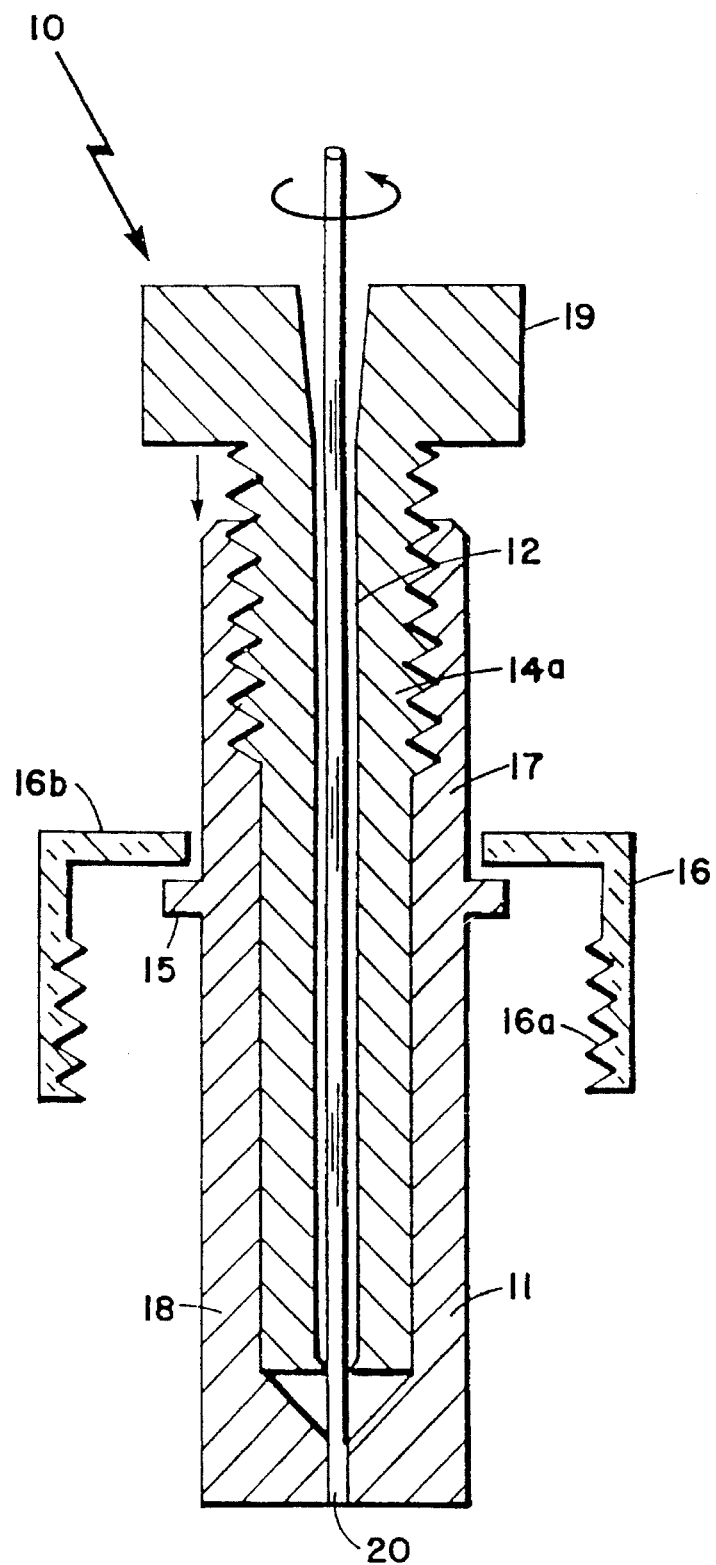
FIG. 1B is a cross-sectional view of a connectorized capillary making use of a compression-type fitting.

Alternatively, as shown in FIG. 1B, the capillary 20 can be firmly but semi-permanently secured within the cavity 12 by means of compression-type or similar fitting 14a sleeved onto the capillary 20 and pressed, threaded (as illustrated), or similarly secured within the cavity 12. When inserted into the cavity 12, the bottom end of the compression fitting 14a tightly secures the capillary 20 by deforming itself around the outer surface of the capillary 20.

A flange 15 is formed in the upper body portion 17. The flange 15, having an outer diameter greater than the outer diameter of the lower portion 18 of the body 11, serves as bearing surface for a nut 16 which is positioned about the body 11.

The nut 16 has internal threads 16a which face the outer surface of at least one section of the lower body portion 18. The nut 16 also includes an upper annular collar 16b having an outer diameter greater than the diameter of the flange 15. The inner diameter of the collar 16b is typically less than the outer diameter of the flange 15, to prevent the collar from moving into the lower portion 18. Thus, when the connector 10 is fastened in place, the upper collar 16b of the nut 16 bears against the flange 15 to hold the connector 10 and hence the capillary tube 20 in place.

Instead of a threads and nuts, it is possible to use other connector fastening arrangements such as the bayonet-type of fastener typically found on electrical "BNC" (baby N-) connectors.

A strain relief 19 is preferably included at the upper body portion 17 to prevent mechanical stresses from bending or breaking the capillary tube 20.

The capillary 20 is typically formed from glass or plastic material similar to those used in manufacturing the outer cladding of fiber optic cables. Extremely thin capillary tubes 20 manufactured to tight tolerances are thus typically available from the fiber optic industry. Nominal inner diameters of approximately 8 to 50 microns can be accomodated to a tolerance of plus or minus five microns, and even tighter tolerances, of less than one micron, are available from the manufacturers of so-called single-mode fiber optic cable connectors. The connectors used may thus also be of the same general construction as those used in the fiber optic industry for interconnecting fiber optic cable.

Figure 1C:
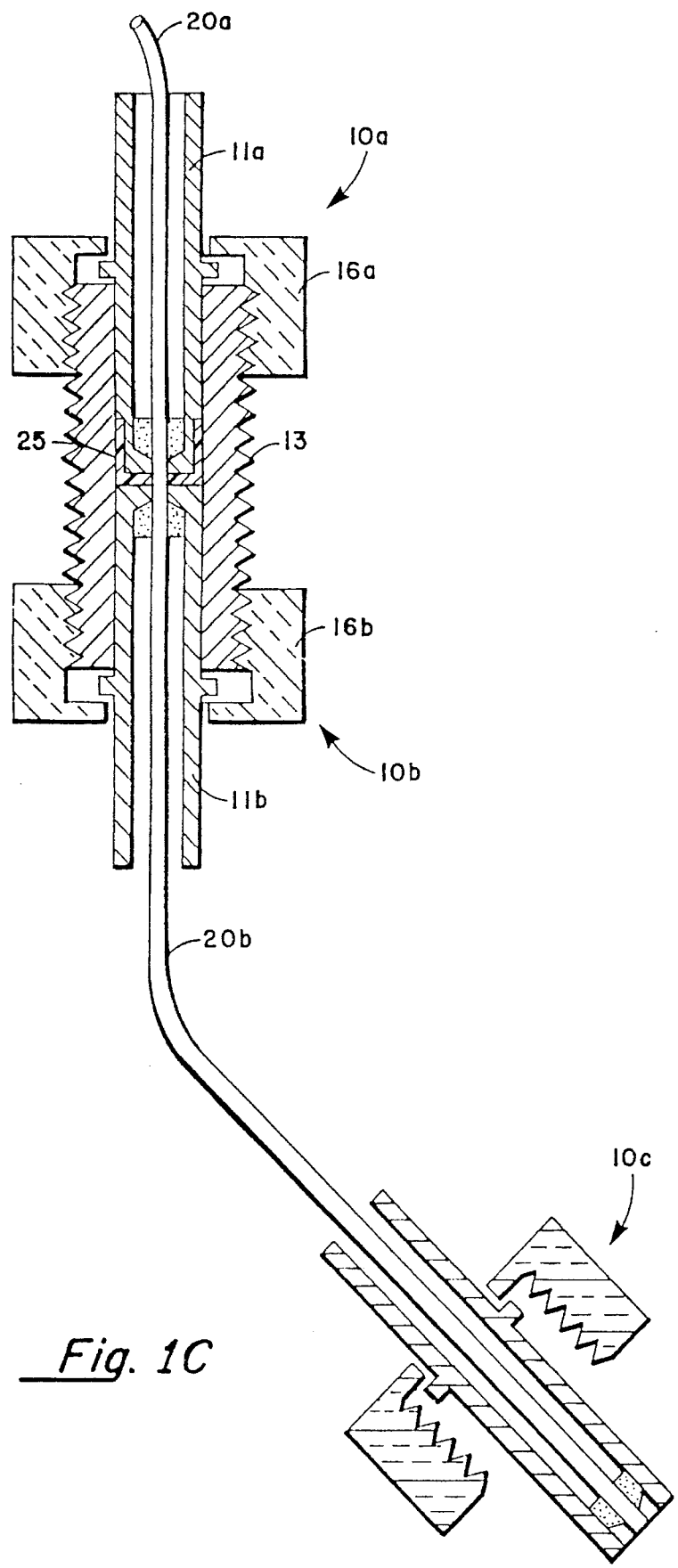
FIG. 1C illustrates how two connectorized capillaries may be connected together, and how a capillary insert may be formed, according to the invention.

The invention 10 permits capillary tubes 20 of various types to be quickly connected and disconnected from one another. For example, as shown in FIG. 1C, two capillaries 20a and 20b may be connected in-line by using a receptacle 13. The first capillary 20a is mounted in a first connector body 11a having a first connector nut 16a. The first nut 16a is connected to the in-line connecting receptacle 13. The second capillary 20b is likewise mounted in a second body 11b having a second nut 16b and secured to the other end of the connecting receptacle 13.

A sealing ferrule 25 made of PTFE or other sealing means is typically disposed between the facing end surfaces of the two connector bodies 11a and 11b.

The connecting receptacle 13 is typically formed of an electrically insulating material.

This arrangement permits simple extensions of a capillary 20a or inserting one or more capillary segments into either end of a main separation capillary.

The two capillaries 20a and 20b may even have different inner diameters, different inside wall coatings, different fillings (such as gel or other packing), or can be composed of different materials. A need to connect capillaries of different types together arises in several different contexts. For example, if the second capillary 20b is coated on the inside with a suitable compound having ion exchange capacity, and if the second capillary 20b is connected to the end of a main separation capillary 20a, but before a detection system, it is possible to achieve chemical suppression of background buffer ions before the detection system is reached. The conductivity detection system is explained in greater detail in connection with FIGS. 4A and 4B.

FIGS. 2A, 2B, and 2C are cross-sectional views of various embodiments of the connector 10, showing the lower portion 18 thereof and in particular the outlet end 9 in greater detail.

The connector 10 shown in FIG. 2A has a capillary 20 which slightly extends beyond the end 21 of the body 11. In this embodiment, the removable sealing ferrule 25 has been attached to the body 11 at the lower portion 18 thereof. The ferrule 25 is used as a sealing device, and is typically formed of PTFE, silicon or other material which is easily deformed under pressure. As will become evident, the electrical insulating properties of the ferrule 25 are sometimes important to consider. The end of the capillary 20 does not normally extend beyond the ferrule 25. In addition, to accommodate the ferrule 25, the end of the lower body portion 18 typically has a reduced diameter section 27 which is at least as long as the length of the ferrule 25.

As shown, the end of the capillary 20 should be aligned with the end 21 of the body 11, radially and axially. The end 21 of the body 11 may be optically polished, if a precision fit of the connector 10 is desired.

The embodiment of FIG. 2B includes an end portion 21 having a sealant coating 22 of PTFE or other sealing material disposed thereon. The coating 22 prevents fluid leaks between connectors 10 and other devices. The sealant coating 22 may be chosen from electrically conductive or non-conductive materials, depending upon the particular application for the connector 10.

FIG. 2C shows a connector 10 having a lower body portion 18 with an external taper 26. This tapered connector is typically used to provide an automatic centering when glass plates are used for capillary interconnection, as later described in connection with FIG. 10.

Figure 3:
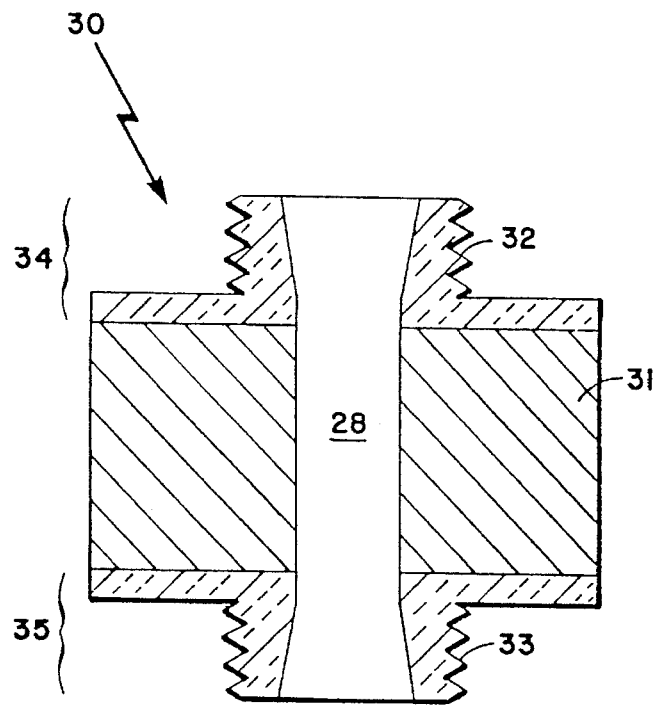
FIG. 3 shows a basic flow cell body having threaded ends which accommodate the connectorized capillaries of FIGS. 1 and 2.

FIG. 3 is a cross-sectional view of a basic instrumentation system component 30 to which the same connectors 10 also mate. The illustrated general form of the system component 30 may be used to implement instrumentation devices such as detectors, valves, reservoirs, and other devices, as will be described below.

The component 30 consists of a body 31, typically formed of an electrically insulating material such as PTFE or ceramic, having an axial cavity 38 formed therein. The component body 31 is attached by suitable means to opposing upper 34 and lower 35 portions.

The upper portion 34 has an externally threaded or bayonet receiving portion 32 designed to mate with the internal thread of the nut 16 or a bayonet, respectively of the connector 10. A similar externally threaded or bayonet receiving portion 33 is likewise disposed on the lower cell portion 35. The upper 34 and lower 35 portions are typically formed of the same material as the body 11 of the connector 10 intended to be used with the particular flow cell 30, to insure a good mechanical as well as electrical connection when required.

It will now be explained how various analytical instrumentation components may be constructed by connecting the capillaries 20 and basic flow cell 30 in different configurations.

Figure 4A:
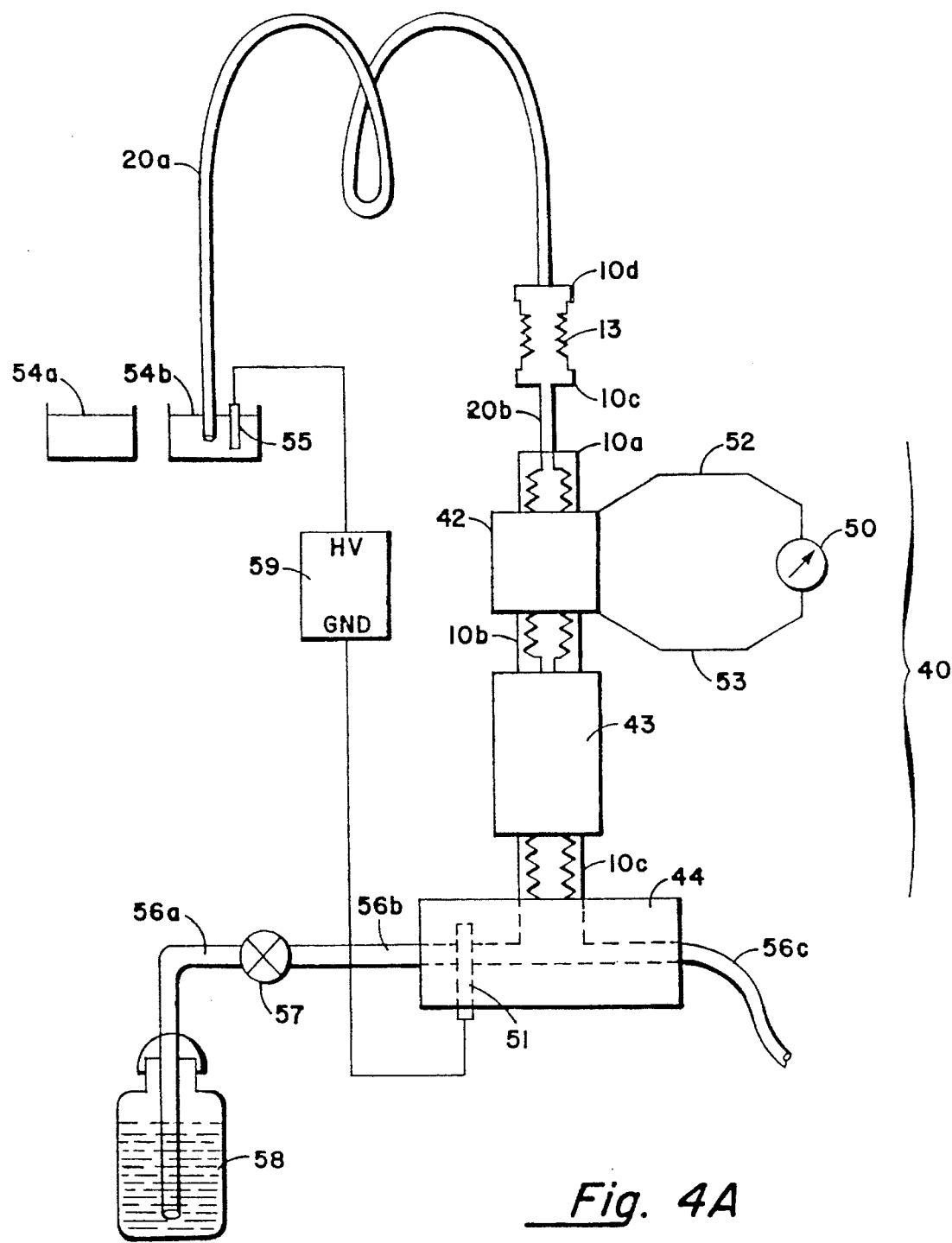
FIG. 4A is an exemplary schematic diagram of a capillary electrophoresis conductivity flow cell detection system.

FIG. 4A shows a capillary zone electrophoresis conductivity flow cell detection system constructed from connectorized capillaries and other components according to the invention. It includes a sample vial 54a, a running buffer vial 54b, a high voltage (HV) power supply 59 having its High Voltage (HV) output connected to an electrode 55 and its ground to a ground electrode 51, a main separation capillary 20a, a main separation capillary connector 10d, an in-line receptacle 13 formed of insulating material, an upper insert capillary connector 10c, a capillary insert (such as an ion exchanger capillary) 20b, a lower insert capillary connector 10a, an in-line conductivity detector 40, various tubing pieces 56a, 56b, and 56c, a flush control valve 57, and a bottle 58 containing buffer solution under pressure.

The in-line conductivity detector 40 consists of various components consisting of a conductivity detection flow cell 42, a conductivity meter 50, a secondary separation capillary holder 43, a ground buffer reservoir cell 44. Each of the components is manufactured as a variation of the basic instrumentation component cell 30 described above.

Figure 4B:
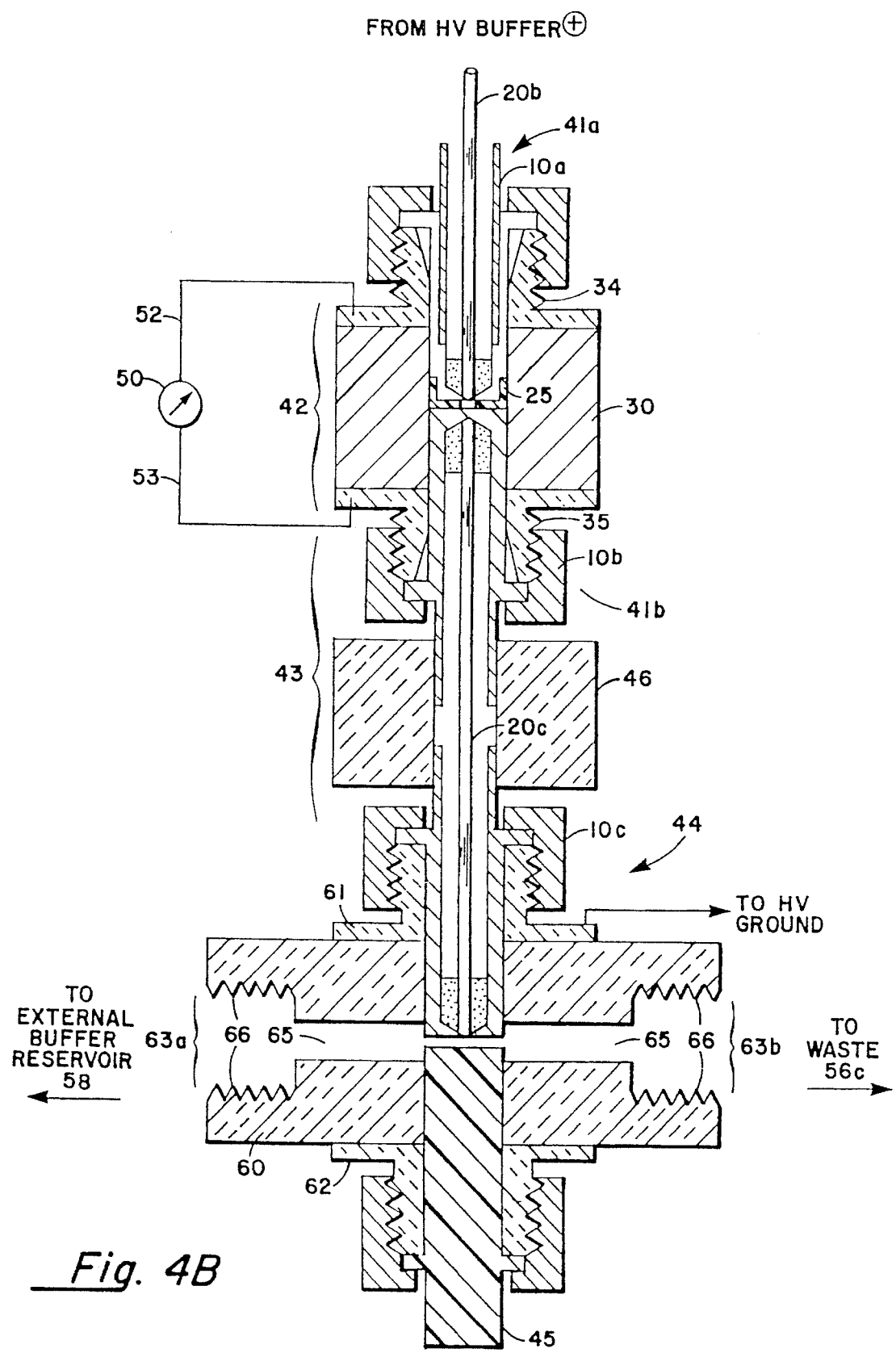
FIG. 4B is a cross-sectional view of an in-line conductivity detector constructed with capillaries and flow cells according to the invention.

FIG. 4B illustrates the components of the in-line conductivity detector 40 in greater detail, including the conductivity flow cell 42, secondary separation capillary holder 43, ground buffer reservoir cell 44, end plug 45, and a conductivity meter 50.

The conductivity flow cell 42 includes a first connectorized separation capillary 41a, a second connectorized separation capillary 41b, and a flow cell 30. The first connectorized capillary 41a consists of a connector 10a and the associated capillary insert 20b. If the capillary insert 20b is not used, then the main separation capillary is inserted in this position.

The second connectorized capillary 41b is similarly formed from a second connector 10b, second separation capillary 20c and a third connector 10c.

By fastening the first connectorized capillary 41a to the upper threaded portion 34 of the flow cell 30, the fluid is presented to the conductivity flow cell 42 from the buffer reservoir 54b (FIG. 4A). By fastening the second connectorized capillary 10b to the bottom threaded portion 35, ionized fluid may exit the cell 30 to the separation capillary 20c.

Electrical connections are provided between the metallic upper cell portion 34 and lower cell portion 35, respectively, to first and second leads, 52 and 53 respectively, of the conductivity meter 50. Leads 52 and 53 may be wire terminals, printed circuit boards, or other electrical connection means.

Because the connectors 10a and 10b are made of metal or metal coated insulators, the conductivity can be detected within the flow cell 42 if the leads 52 and 53 are arranged as shown.

The separation capillary holder 43, consisting of an insulator tube 46, is designed to mechanically support the connectors 10b and 10c, which in turn couple the separation capillary 20c to the grounded buffer solution reservoir 44. The insulator tube 46 is formed as a hollow, open cylinder of a suitable insulating material, PTFE or plastic being an appropriate choice, to maintain electrical isolation between the connectors 10b and 10c. The inner diameter of the insulator tube 46 is chosen to be approximately the same as the outer diameter of the connectors 10b and 10c.

The buffer reservoir cell 44 consists of a buffer cell body 60 typically made of insulating material, a buffer cell upper flange 61, an optional buffer cell lower flange 62, a reservoir inlet 63a, a waste outlet 63b, and an optional end plug 45.

The buffer cell upper flange 61 includes a hole that accommodates the third connector 10c. Similarly, the buffer cell lower flange 62 accommodates the end plug 45. The end plug 45 may be a sealing dummy connector through which no fluid flows, or a connectorized sensor may be inserted in the place of the end plug 45, to detect changes in the buffer zones as it flows out the end of capillary 20c. In addition, the end plug 45 may be a metal insert providing a high voltage (HV) ground connection directly into the cavity 65.

The ground buffer cell body 60 is connected to buffer reservoir and waste by means of connectorized tubing as shown in FIG. 4A. The tubing 56 is attached to the outlets 63a and 63b by means of threaded portions 66. An inner cavity 65 thus contains buffer fluid to form a ground buffer reservoir, or at least part of one, depending upon whether or not the HV ground electrode 51 is contained within buffer cell body 60.

As shown in FIGS. 4A and 4B, the HV ground electrode 51 can also be introduced into the buffer cell body 60 either by means of a connector body 10c constructed of a suitable conductive material such as stainless steel, together with a conductive flange 61 making contact to it, made of some other suitable material such as platinum, at a suitable place within cavity 65. In either case, a connection is made to the HV ground reference point.

Alternatively, the HV ground electrode can be external to the ground buffer cell body.

As evident from FIG. 4A, it is thus possible to refresh the ground buffer solution contained within cavity 65 at will, by means of flushing new buffer solution from the external buffer reservoir 58 through tubing 56a and 56b, by operating the valve 57. Any contaminated buffer fluid from the cavity 65 is then horizontally flushed to a waste reservoir through outlet 63b (FIG. 4B) and tubing 56c.

It is also possible to provide multiple detection simultaneously, by placing one or more additional detectors, holders and capillary segments of various types, in-line, after the capillary holder 43, but before the reservoir cell 44.

Figure 5A:
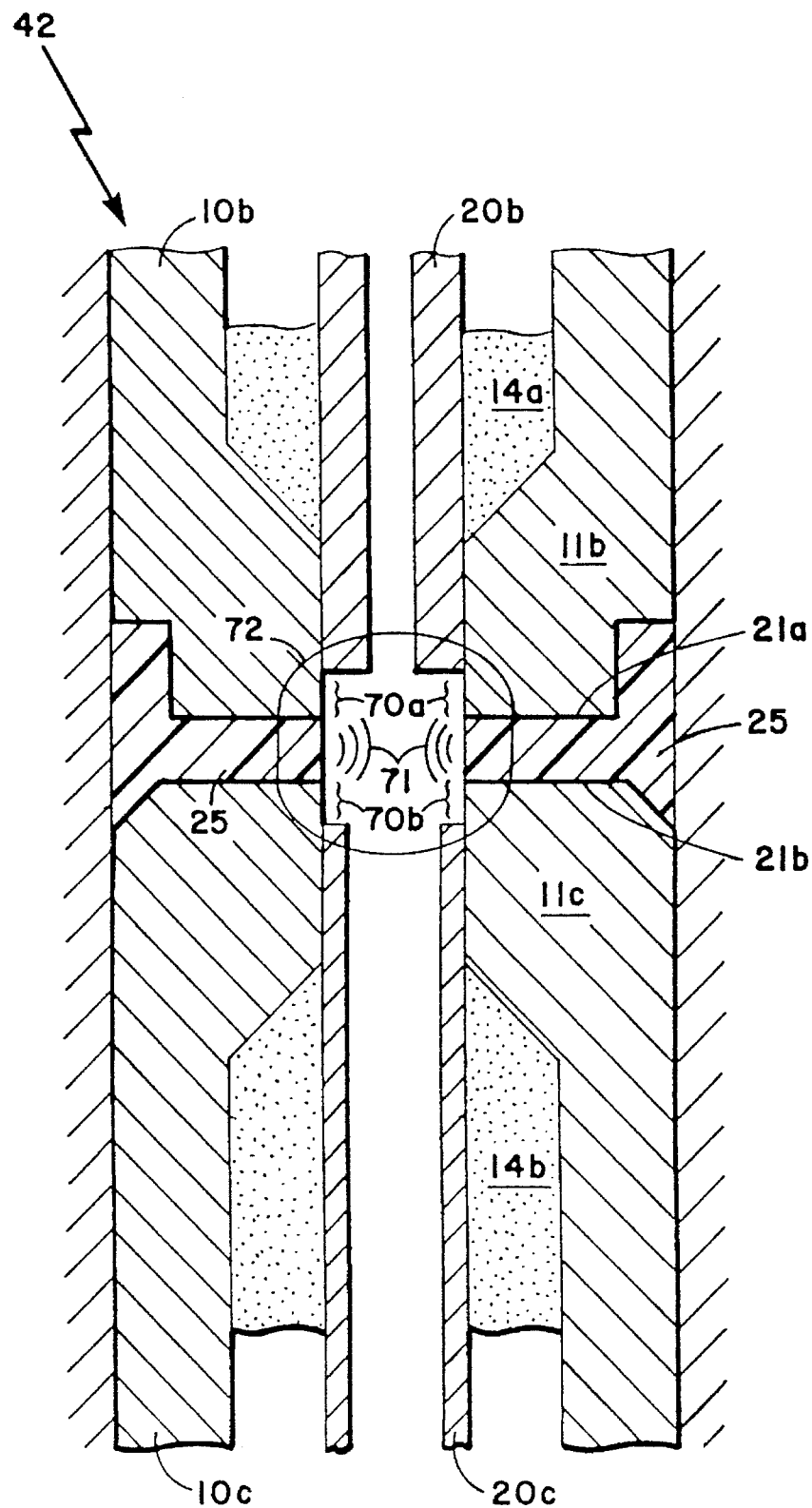
FIGS. 5A and 5B are more detailed cross-sectional views of the conductivity flow cell.

FIG. 5A is a more detailed view of one embodiment of the conductivity flow cell 42. The first separation capillary 20b has a relatively small inner diameter, on the order of 50 microns. The second separation capillary 20c is typically of a larger inner diameter, such as 75 microns. This diameter difference is to reduce potential difference across the capillary 20c, developed due to current flow in the capillary. This somewhat simplifies electrical requirements imposed on conductivity detector circuitry, since it has to "float" at fairly high voltage above the HV ground (typically 2 to 3 KV).

The first separation capillary 20b and second separation capillary 20c are purposefully drawn back, away from the respective ends 21a and 21b of their associated stainless steel connector bodies 11b and 11c, to expose upper 70a and lower 70b annular sensing surfaces. Recall that the sensing surfaces 70a and 70b are respectively electrically connected to the conductivity meter 50 by means of electrical, conductive connector bodies 11b and 11c and electrically conductive upper portions 34 and 35.

In this view, the ferrule 25 is shown in a slightly deformed state, since the connectors 10a and 10b are firmly attached to the body 30 thus pressing against the ferrule 25. The ferrule 25 provides electrical insulation between the first 10a and second 10b connectors as well as fluid isolation, to insure that all fluid travels towards the ground buffer and not out towards the sides of the body 30.

A dead volume 72 is encompassed by the first separation capillary 20b and second separation capillary 20c, the upper sensing surface 70a, lower sensing surface 70b, and ferrule 25.

The sensing surfaces 70a and 70b must be short enough so as not to cause electrolysis due to the voltage drop in the buffer solution. Such a condition could possibly cause bubbles in the buffer fluid, which can in turn interfere with conductivity measurements. A typical desired thickness for the surfaces 70a and 70b is approximately no more than 50 microns, to avoid such bubble formation. In order to minimize the dead volume 72, the capillaries 20b and 20c should have a small outer diameter (typically around 150 microns). This also increases the sensitivity of zone detection due to a fact that the measuring field 71 more fully extends into the zones as they migrate from capillary 20b to capillary 20c.

Figure 5B:
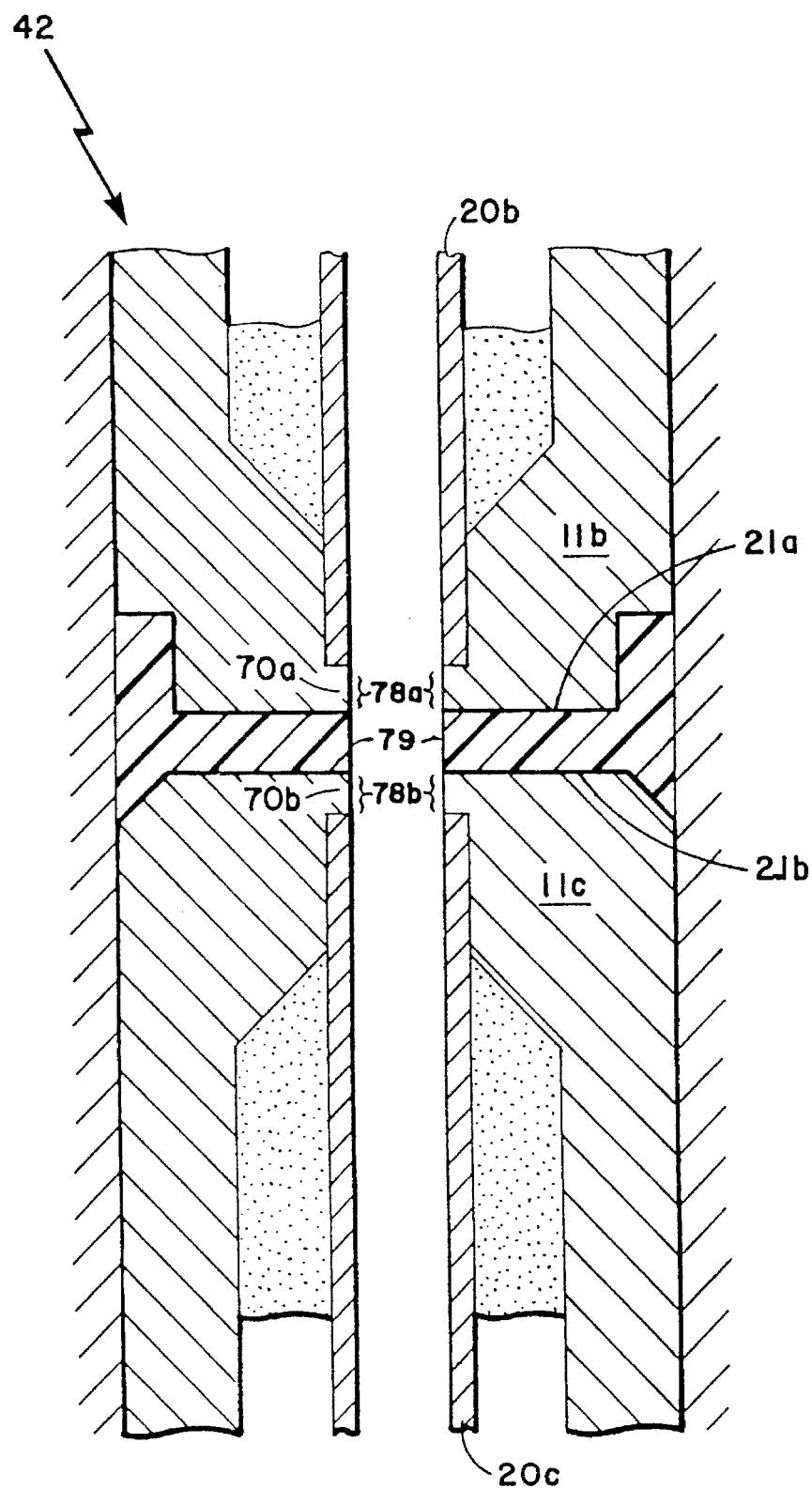

FIG. 5B is an alternate embodiment of the conductivity flow cell 42 which has a negligible dead volume 72. This is accomplished by forming an inner annulus 78a on body 11b, at the end 21a of first connector 10a. A similar annulus 78b is formed at the end of body 11c. The annuli 78a and 78b are of the same approximate inner diameter as 79 of the ferrule 25. This reduces the diameter of the outlets 13a and 13b to approximately the same as the inner diameter of capillaries 20b and 20c, as well as the ferrule 25, thereby minimizing dead volume.

Minimization of the dead volume 72 is important in certain applications, such as when the zones to be detected are spaced close together. The larger the dead volume, the greater the likelihood that a portion of zone may quickly find its way into the dead space, but take longer to exit from the dead space. If such statistical spreading (peak tailing) of the time it takes for a given zone to exit the flow cell 30 approaches the magnitude of the time difference between different zones of interest, the tail of one zone may be exiting the flow cell 30 at the same time as the main portion of a succeeding zone is entering the flow cell 30, thereby making it difficult or impossible to accurately separate successive zones.

Figure 6A:
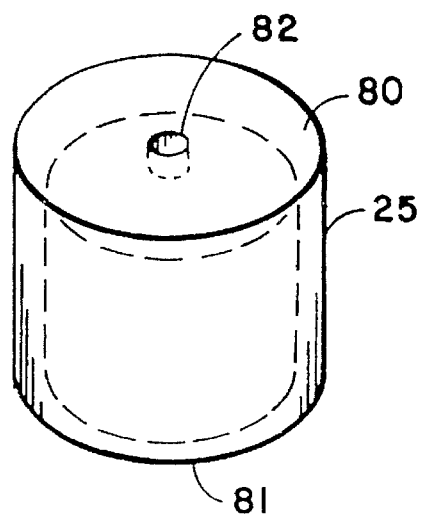
FIGS. 6A is a perspective view of a ferrule used with the connectorized capillaries in certain applications.

FIG. 6A is a perspective view of the ferrule 25. It is generally cylindrical in shape, having a closed upper end 80 and open lower end 81. The upper end 80 has a hole 82 formed therein. The size of the hole 82 determines the inner diameter of the annulus 79 of FIG. 5A and 5B.

Figure 6B:
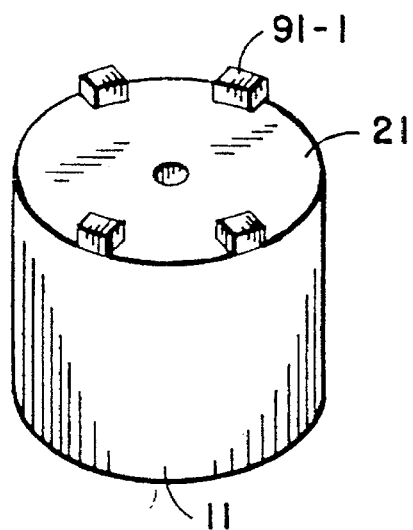
FIGS. 6B and 6C are perspective views of various connector tip geometries used in certain other applications.
Figure 6C:
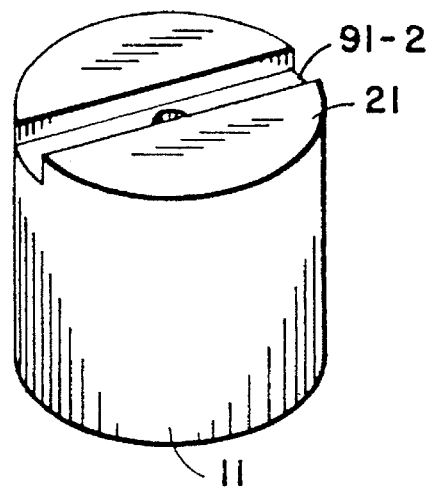
Figure 7A:
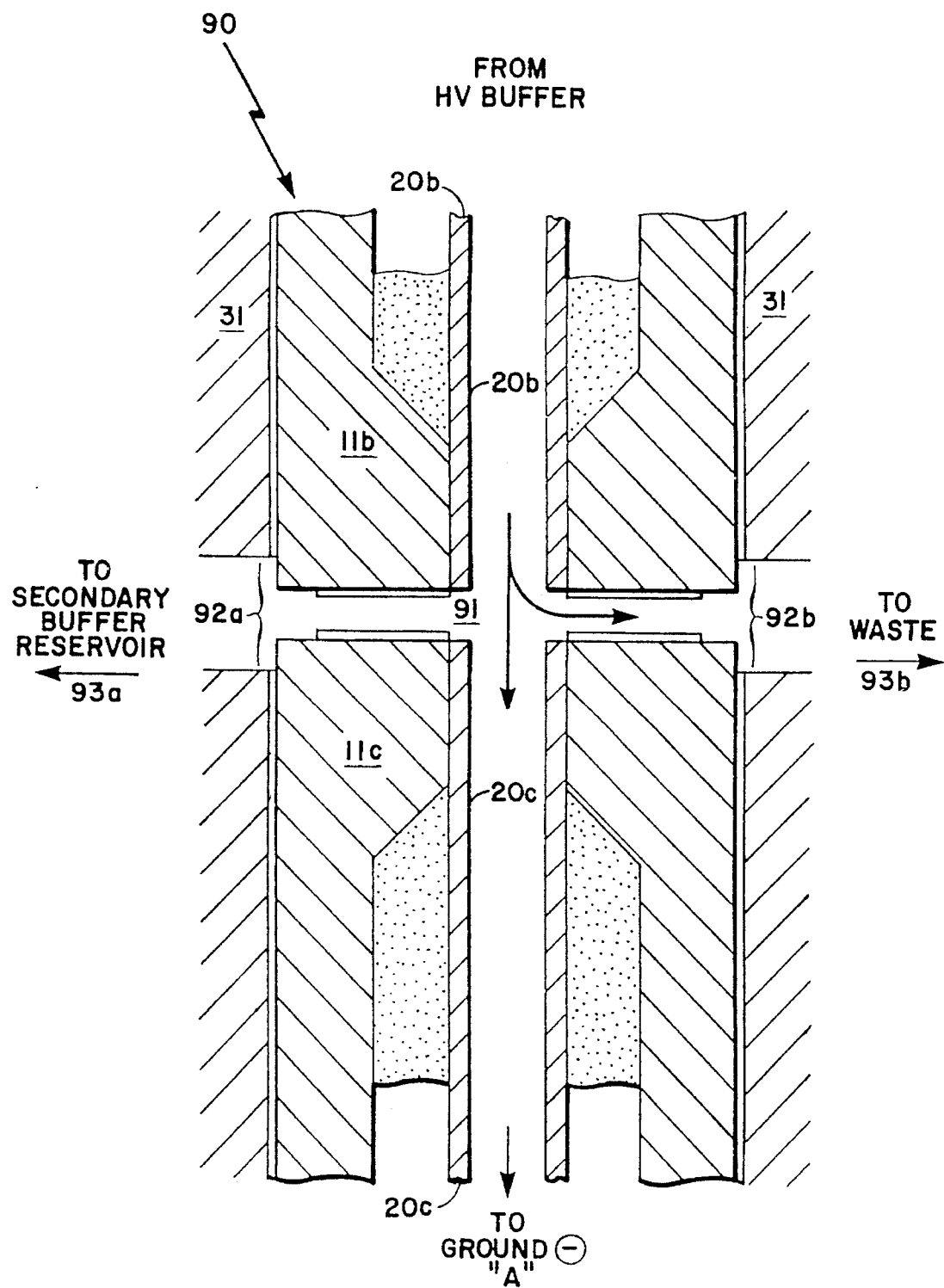
FIG. 7A is a detailed cross-sectional view of a discrete separation valve which makes use of the connector tip geometries shown in FIG. 6B and 6C.

FIG. 6B and 6C are perspective views of end portions 21 of the connector body 11 which may be used to form a channel in a discrete separation valve embodiment of the invention. FIG. 7A illustrates an embodiment of the flow cell 30 which functions as a discrete separation valve 90, in particular. This component permits incoming ionized fluid to be steered to the second separation capillary 20c or to a side outlet 93b.

The bodies 11b and 11c of the valve 90 are typically formed of ceramic or other electrically insulating material. One of the bodies has a shape described in FIGS. 6B or 6C while the other typically has a flat surface as in FIG. 2A.

A cross-flow channel 91 is created by contacting 11b and 11c and is positioned in between transverse openings 92a and 92b in the cell body 31. The channel 91 is connected to a source of buffer solution through opening 92a, and is typically on the order of 10–100 microns deep.

The cross-flow channel 91 may be formed by appropriately formed castleations 91-1 on the end 21 of the body 11, as shown in FIG. 6B, or as a radial groove 91-2, as shown in FIG. 6C.

When there is little or no cross-flow in the channel 91, any ions entering the valve 90 from the first separation capillary 20b will pass to the second separation capillary 20c, as for the other system components 30 previously described. However, when there is a sufficient cross-flow in the channel 91 emanating from opening 92a, the solution emerging from capillary 20b is steered towards the side outlet 92b, along with the cross-flow.

The ion steering in the channel 91 can be pressure- or electrically-induced.

In the later case, the 'position' of the valve is chosen by grounding either a buffer solution reservoir connected to the bottom end of the second separation capillary 20c, or by grounding a splitter buffer reservoir connected to the side outlet 93a or 93b.

Figure 7B:
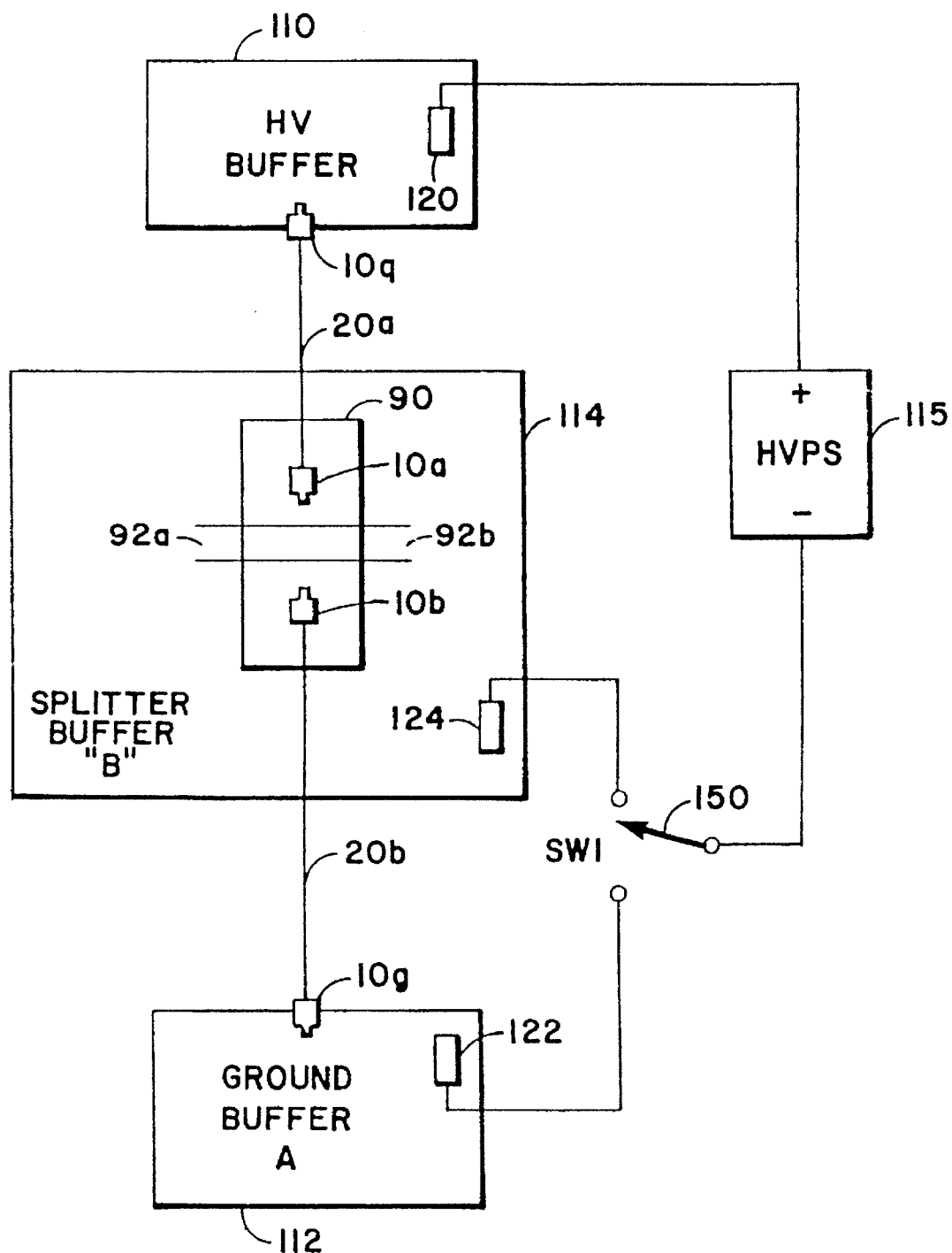
FIG. 7B is a schematic diagram of an electrically controlled discrete separation valve utilizing the connector tips shown in FIG. 6B or 6C.

In particular, as shown in the electrical schematic diagram of FIG. 7B, the first separation capillary 20a provides fluid connection between a high voltage buffer reservoir 110 and the valve 90. The high voltage buffer 110 is connected to the high voltage terminal of a high voltage power supply 115 (typically 30 thousand volts) via an electrode 120.

The second separation capillary 20b connects the valve 90 to a first ground buffer (A) 112. Buffer 112 is electrically connected to a lower terminal of a switch 150 via an electrode 122.

The fluid channel 91 of the valve 90 is connected to a splitter buffer (B) 114. The splitter buffer 114 is electrically connected to the upper terminal of the switch 150 via an electrode 124. The remaining common terminal of the switch 150 is connected to the ground terminal of the power supply 115.

To electrically operate the valve 90, the position of the switch 150 is simply flipped. For example, when the switch 150 is in the lower position, zones and buffer fluid are enabled to flow from the first separation capillary 20a to the second separation capillary 20b. When the switch 150 is in the upper position, the outlet flow from first separation capillary 20a is sent to the splitter buffer 114, since the ground reference is then in the splitter buffer 114 and not in the buffer (A) 112.

Figure 8A:
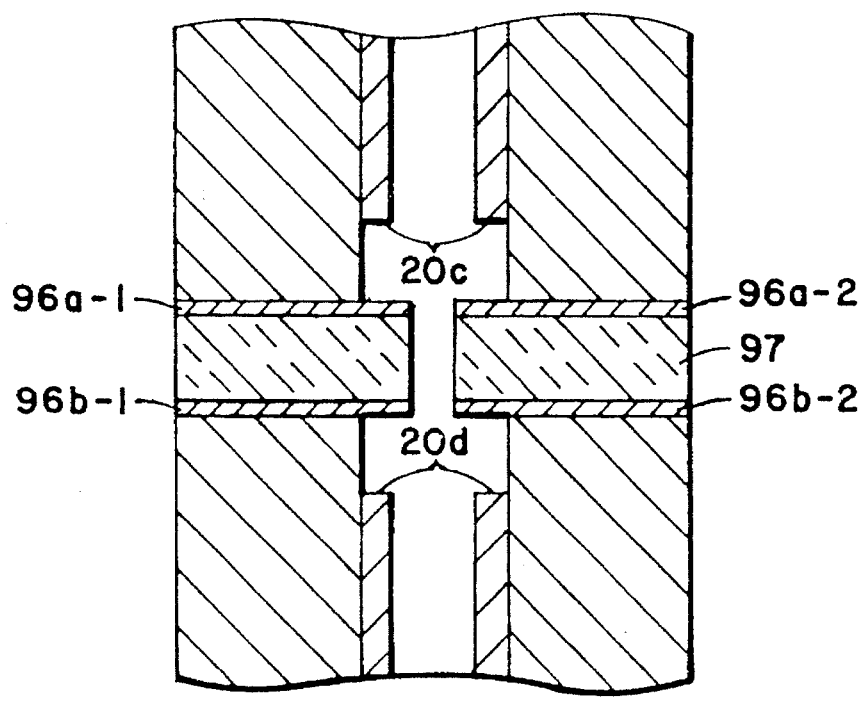
FIGS. 8A and 8B are cross-sectional and perspective views of a gasket which can be used in the flow cell.
Figure 8B:
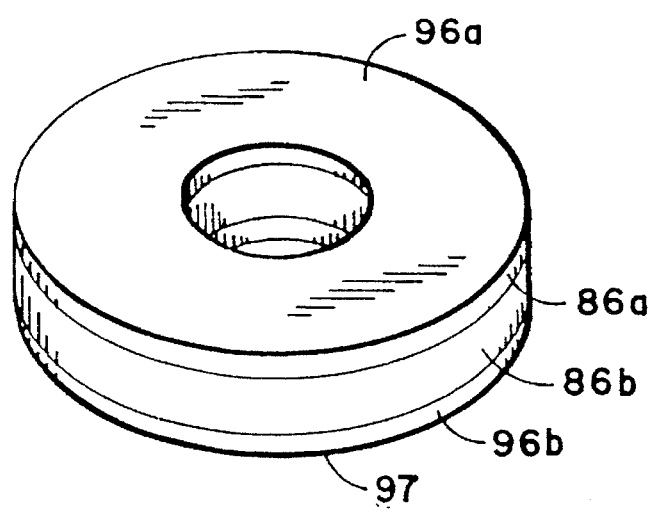

FIGS. 8A and 8B illustrate an alternative embodiment of a conductivity flow cell 42 using a ring gasket 95 instead of a ferrule 25. This gasket 95 provides sealing between surfaces 21a and 21b as well as a means of providing two mutually insulated conductive sensing surfaces 96a and 96b, which are in turn connected to the conductivity meter 50 (FIG. 4A). This gasket can also have a different shape, such as that of the ferrule 25.

Conductive surfaces 96a and 96b are formed typically by depositing conductive films 86a and 86b on opposing surfaces of an insulating body 97. The sensing is performed only by the portions of the surfaces 96a and 96b which extend into the solution between ends of the capillaries 20c and 20d.

Figure 9A:
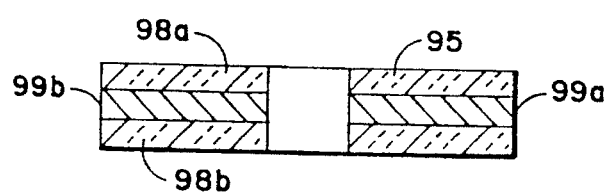
FIGS. 9A and 9B illustrate an alternate embodiment of the gasket.
Figure 9B:
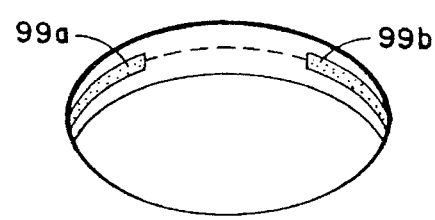

FIG. 9A and 9B illustrate another embodiment of the gasket 95 formed by fusing wires, or other conductive elements 99a and 99b between two ring-shaped insulators 98a and 98b together. This embodiment has an advantage that the conductivity sensing is performed across the flow rather than axially.

Figure 10:
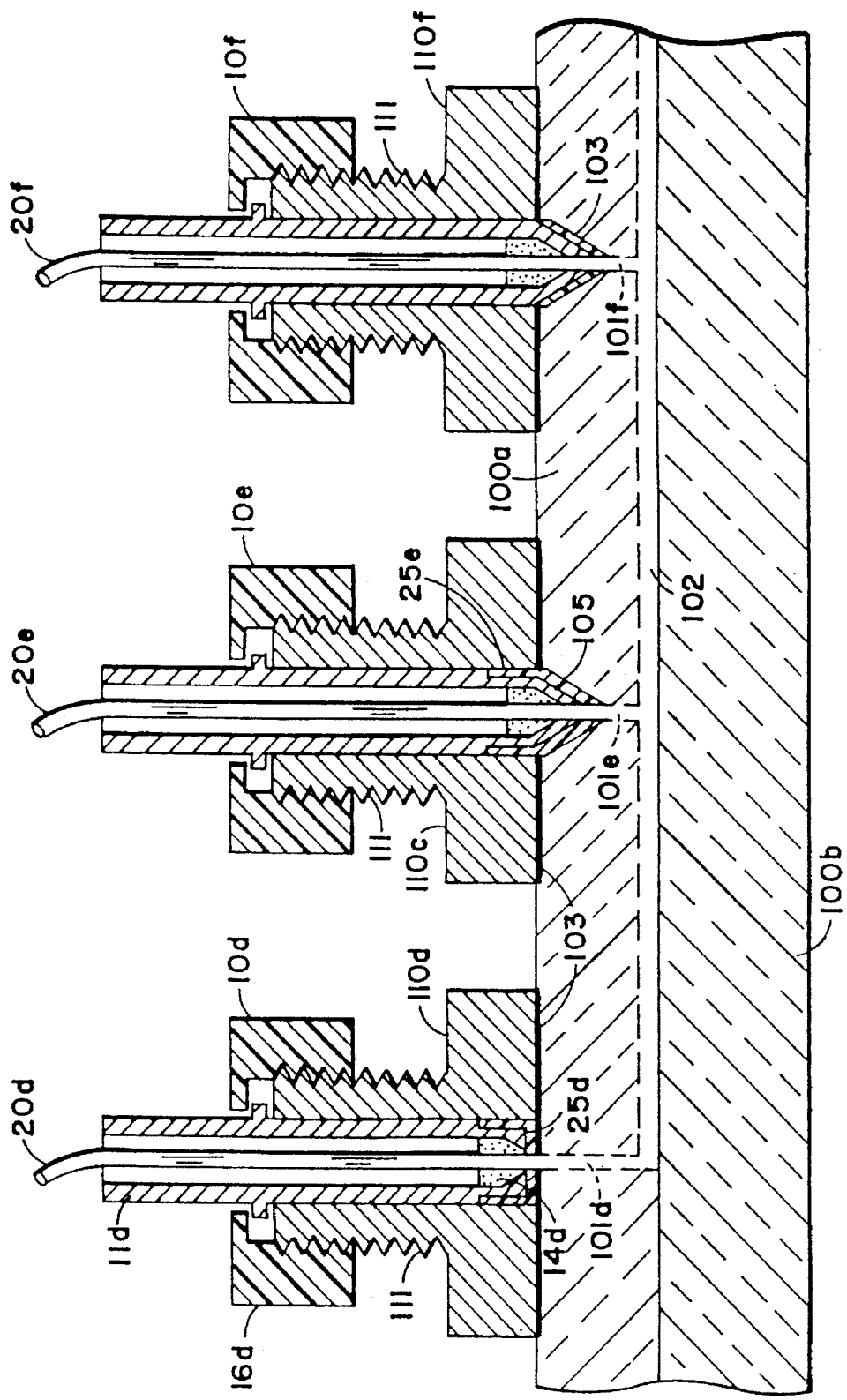
FIG. 10 is a cross-sectional view of the various types of connectorized capillaries interconnected by a glass plate.

FIG. 10 shows how various types of connectors 10 may be used with glass plate-type channels. Such channels provide a convenient mechanism for separation or interconnection of two or more capillaries 20d, 20e, and 20f.

A horizontal channel 102 is typically formed by fusing a pair of etched plates 100a and 100b, the plates being typically formed of glass but possibly from other materials such as plastic. The channel 102 may consist, as shown, of a thin, shallow etched groove formed in a top plate 100a. However, other arrangements are possible, where the channel 102 is formed entirely in one plate or the other.

Holes 101d, 101e, and 101f are formed in the top or bottom plate, typically oriented perpendicularly to the channel 102, to permit access to the channel 102 by connectors 10d, 10e, and 10f respectively.

A sealing surface 103 of PTFE or other sealing material may be formed on the top of the top plate 101a. Sealing material may also be contained on contacting surfaces at connectors 10d, 10e, or 10f.

The connector 10d is of the type shown in FIG. 2A, having its own sealing surface disposed on its bottom end 21 in the form of a ferrule 25d. Connector 10d is positioned so that the capillary tube 20d is held in place and concentrically aligned with the hold 101d in the plate by a surface-mountable 110d which mates with the connector 10d.

Alternatively, a connector 10e may be used which is of the tapered, self-centering type similar to that described in FIG. 2C. Connector 10e mates with another surface-mountable receptacle 110e. Here, a corresponding taper 105 is also formed in the hole 101e in the top plate 100a. A tapered ferrule 25e provides sealing, if desired.

The connector 20f, also of the self-centering type, makes use of sealant 103, which is preferably run into the tapered hole 101f.

The use of a tapered hole 101e or 101f and matching tapered connectors 10e and 10f greatly expedites alignment of the capillary and holes, which, the reader will recall, are typically only 50 microns in size.

The glass channel structure illustrated in FIG. 10 can also be used to implement a detection system between the various connectors 10d, 10e and 10f. The detectors can be of either conductivity, electrochemical, ultraviolet (UV), visible (VIS) or other types. Conductivity and electrochemical detectors can also be implemented by depositing suitable electrodes on surfaces contained within channel 102. UV or VIS detection can be accomplished by shining light through the glass structure either perpendicularly to the channel 102 or axially along the channel 102. In case of UV or VIS there is a distinct advantage in this arrangement, since the channel 102 can be shaped or sized to enhance the detection sensitivity in the detection area only.

Because of the invention, it is also now easier to design optics to interface with the fluid contained between flat glass surfaces rather than cylindrical surfaces (capillaries 20) as it is commonly done presently.

The structure in FIG. 10 can also be used as a interconnecting structure between multiple connectors 10 and a buffer ground beaker. The advantage with this structure is that the detection system can be wholly contained within it, by means of electrodes deposited in the channel 102. Similarly, since it can be made of transparent material, the customarily required UV/VIS or fluorescence detection in CZE instrumentation can be implemented by passing light through the glass plate structure as described earlier.

Figure 11A:
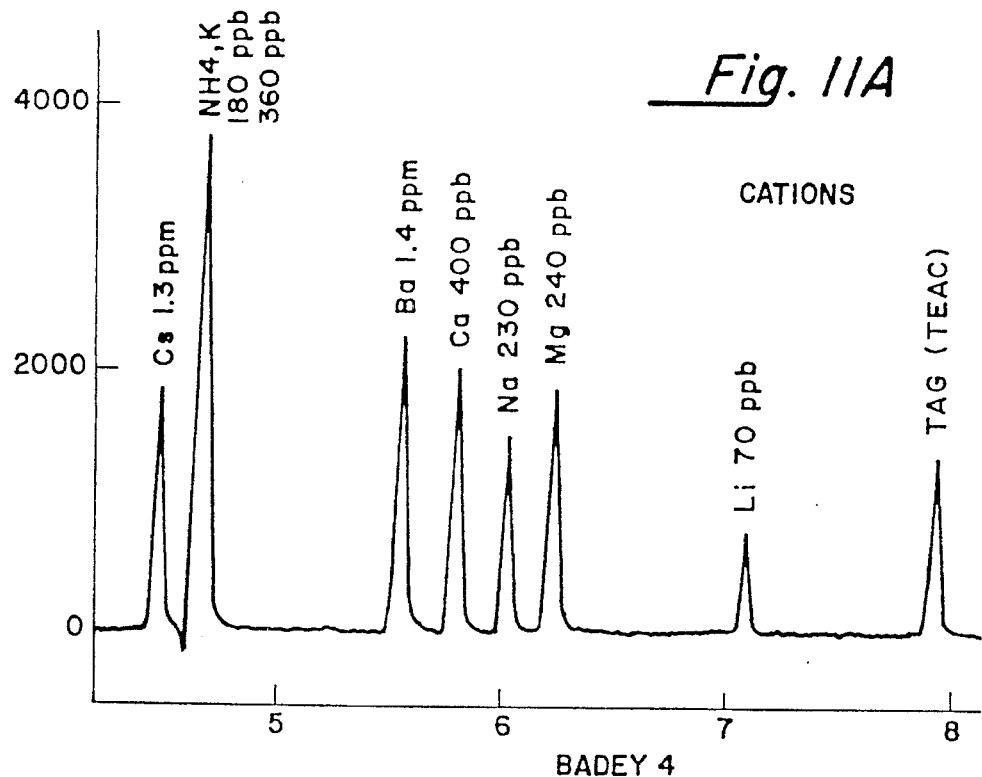
FIGS. 11A and 11B are electropherograms of small inorganic ion separations in-line conductivity flow cell detector according to the invention.
Figure 11B:
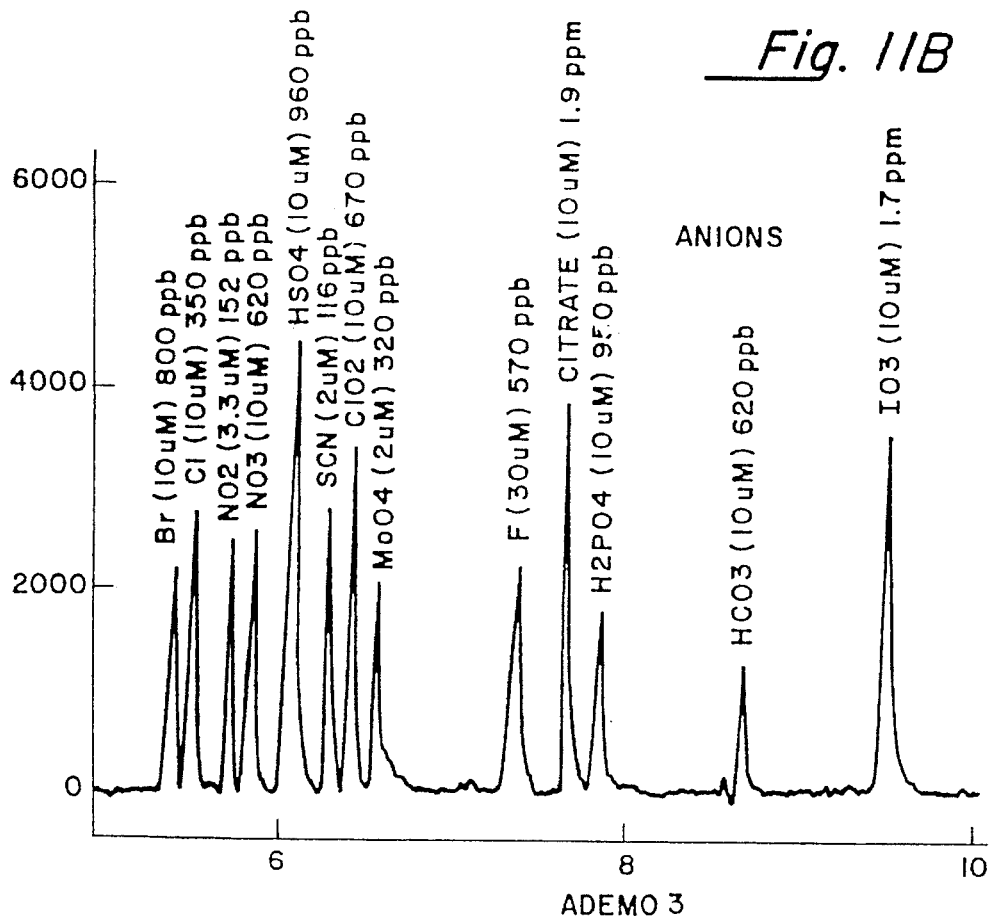

FIGS. 11A and 11B are electropherograms of small inorganic ion separations in-line conductivity flow cell detector according to the invention. FIG. 11A is the results using 30 milli-Molar HIS-MES buffer solution, and FIG. 11B is using 50 milli-Molar CHES-LiOH buffer solution.

The terms and expressions which have been employed above are used as terms of description and not meant to be limiting in any way, and there is no intention to exclude any equivalents of the features shown and described or portions thereof, and it should be recognized that various modifications are possible while remaining within the scope of the invention as claimed.

What is claimed is:

1. A device for interconnecting a capillary tube to a conductivity flow cell used in a separation instrument comprising:

a connectorized capillary consisting of a body having an internal cavity, the cavity running in parallel with the major axis of the body and tapering to a body end portion, the cavity having an outlet opening adjacent the tapered body end portion, the cavity having a capillary tube fastened therein, the body also having an annular threaded fastener disposed about an exterior surface of said body, and the body also having electrically conductive external surfaces;

a receptacle including a conductivity flow cell for performing separation instrumentation functions, the receptacle for accepting the body of the connectorized capillary, the receptacle including threaded portions for engaging the threads on the fastener of the connectorized capillary; and means for electrically connecting the connectorized capillary to the conductivity flow cell, the external surfaces of the body of the connectorized capillary thereby providing electrical contact to the conductivity flow cell.

2. A device as in claim 1 wherein the receptacle is interconnected between two connectorized capillaries, and the bodies of the two connectorized capillaries each have electrically conductive external surfaces, and wherein the device additionally comprises:

means for electrically connecting each such connectorized capillary to the conductivity flow cell, the body of each connectorized capillary providing electrical contact to the conductivity flow cell; and conductivity meter having two contacts, the conductivity meter being connected to the conductivity flow cell by connecting the first contact to one surface of the conductivity flow cell, and by connecting the second contact to another opposing surface of the conductivity flow cell.

3. A device as in claim 2 wherein the receptacle also serves as a discrete separation valve including a transverse channel disposed transverse to a longitudinal axis of the conductivity flow cell.

4. A device as in claim 3 wherein the receptacle is connected to a buffer solution reservoir, and wherein the device additionally comprises:

means for introducing a transverse flow of the buffer solution into the transverse channel of the discrete separation valve.

5. A device as in claim 2 wherein the conductivity flow cell comprises:

a gasket having two opposing conductive surfaces which provide sealing between the electrically conductive external surfaces of the two connectorized capillary bodies, the two opposing conductive surfaces of the gasket being connected to the conductivity meter.

6. A device as in claim 5 wherein the two opposing conductive surfaces of the gasket are formed by fusing a central conductive member and two outer insulating members.

7. A device as in claim 1 additionally comprising a ferrule, adapted to be placed over the tapered end portion of the connectorized capillary.

8. A device as in claim 7 wherein the ferrule is electrically insulating.

9. A device as in claim 1 wherein the end of the capillary tube adjacent the outlet opening is drawn back from the outlet opening to provide an annular conductivity sensing surface inside the body of the connectorized capillary.

10. A device as in claim 1 wherein the tapered end portion of the body adjacent the outlet opening has a transverse channel formed on the periphery thereof, the transverse channel being oriented transverse to a longitudinal axis of the capillary tube.

11. A device as in claim 1 wherein the body has a castleated surface adjacent the tapered end portion.

12. A device as in claim 1 wherein the receptacle is connected to a buffer solution reservoir, and wherein the device additionally comprises:

means for switching a ground reference electrode disposed within the buffer solution reservoir.

13. A device as in claim 1 additionally comprising a strain relief guide surrounding the outside of the capillary tube adjacent the end of the body opposite the outlet opening.

14. A device as in claim 1 wherein the receptacle also serves as a valve.

15. A device as in claim 1, wherein a sealant coating is placed on the tapered end portion of the body adjacent the outlet opening.

16. A device as in claim 15 wherein the sealant coating is electrically insulating.

* * * * *